United States Patent [19]

Kruse et al.

[11] Patent Number: 4,782,061

[45] Date of Patent: Nov. 1, 1988

[54] A METHOD OF TREATING PSYCHOTROPIC CONDITIONS EMPLOYING SUBSTITUTED PIPERAZINE COMPOUNDS

[75] Inventors: Cornelis G. Kruse; Johannes A. M. van der Heyden; Ineke van Wijngaarden; Jan Hartog; Berend Olivier, all of Weesp, Netherlands

[73] Assignee: Duphar International Research B.V., Weesp, Netherlands

[21] Appl. No.: 810,207

[22] Filed: Dec. 18, 1985

[30] Foreign Application Priority Data

Dec. 21, 1985 [NL] Netherlands .......................... 8403918

[51] Int. Cl.$^4$ ........................................... A61K 31/495
[52] U.S. Cl. ..................................... 514/254; 544/230; 544/363; 544/366; 544/372; 544/373; 544/376; 544/377
[58] Field of Search ............... 544/363, 366, 372, 373, 544/376, 377, 230; 514/254

[56] References Cited

U.S. PATENT DOCUMENTS

| | | | |
|---|---|---|---|
| 4,062,870 | 12/1977 | Watts | 544/373 |
| 4,105,664 | 8/1978 | Gerecke et al. | 544/372 |
| 4,355,031 | 10/1982 | Demerson et al. | 544/373 |
| 4,404,383 | 9/1983 | Dunlop | 544/379 |
| 4,426,380 | 1/1984 | Wenk et al. | 544/376 |
| 4,558,043 | 12/1985 | Wenk et al. | 544/376 |

FOREIGN PATENT DOCUMENTS

| | | |
|---|---|---|
| 0048045 | 3/1982 | European Pat. Off. . |
| 2496662 | 6/1982 | France . |
| 2086896 | 5/1981 | United Kingdom . |
| 2097790 | 11/1982 | United Kingdom . |

OTHER PUBLICATIONS

Otsuka Pharm KK Saka 22.05.81 J57193-459.
J. Chem. Soc., (C), No. 10 (1967), pp. 1003-1006.

Primary Examiner—Richard L. Raymond
Assistant Examiner—James H. Turnipseed
Attorney, Agent, or Firm—Stevens, Davis, Miller & Mosher

[57] ABSTRACT

The invention relates to a group of new bicyclic heteroarylpiperazine derivatives of formula 1. It was found that these compounds have interesting psychotropic in particular anti-psychotic properties.

The compounds can be prepared according to methods known for the synthesis of analogous compounds.

2 Claims, No Drawings

A METHOD OF TREATING PSYCHOTROPIC CONDITIONS EMPLOYING SUBSTITUTED PIPERAZINE COMPOUNDS

The invention relates to new pharmaceutical compositions having interesting psychotropic properties, notably antipsychotic properties, to new bicyclic heteroaryl piperazine derivatives which can be used in such compositions as the active substance and to the preparation of these compositions and compounds.

It was found that compounds of the general formula 1

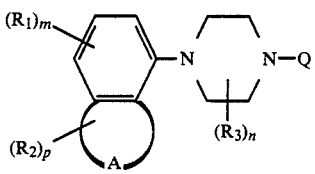

in which
- —A together with the two carbon atoms of the phenyl group forms an entirely or partly unsaturated cyclic group having 5–7 ring atoms with in the ring 1–3 hetero atoms from the group O, S and N, with the proviso that the sum of the number of oxygen atoms and sulphur atoms is at most 2, and that the nitrogen atoms in the ring may be substituted with a group $R_4$ which may be hydrogen, alkyl, hydroxyalkyl or acyl;
- —Q is an optionally branched or cyclic, saturated or (poly)unsaturated alkyl chain which may comprise one or more atoms from the group O and N in the chain or terminally and in which carbonyl groups, thiocarbonyl groups, sulphinyl groups or sulphonyl groups may also be present; the chain may moreover be substituted with one or more halogen atoms or with one or more optionally substituted phenyl groups, heteroaryl groups or heterocyclic groups; if the chain comprises a nitrogen atom, this is substituted with at least one group $R_5$ which is an optionally substituted phenyl group or an alkyl group, cycloalkyl group, hydroxyalkyl group;
- —$R_1$ and $R_2$ may be alkyl, cycloalkyl, optionally substituted phenyl or heteroaryl, hydroxyalkyl, alkoxyalkyl, alkoxy, aryloxy, alkylthio, arylthio, mono- or dialkylamino, mono- or diarylamino, hydroxyl, amino, alkyl-, alkoxy- or amino, or mono- or dialkylaminocarbonyl, nitro, cyano, halogen, trifluoromethyl, trifluoromethoxy, alkyl- or amino- or mono- or dialkylaminosulphonyl; $R_2$ may moreover be an oxo group or thioxo group; m has the value 0–3 and p has the value 0–2; and
- —$R_3$ is an alkyl group and n has the value 0–2, and the acid addition salts and prodrugs thereof have interesting psychotropic properties.

Compounds which are to be preferred on the basis of their properties are compounds of formula 1, in which the the symbols have the following meanings:
- —A forms together with the two carbon atoms of the phenyl group an entirely or partly unsaturated ring consisting of 5-atoms, which ring comprises at least one oxygen atom;
- —Q is straight, branched or cyclic alkyl, alkenyl, alkynyl, alkoxy- or hydroxyalkyl, aryl- or heteroarylalkyl, or a group of the formula —D—$NR_5$—CO—$R_6$, in which D is an optionally branched alkyl chain having at most 8 carbon atoms, $R_5$ has the above meaning, and $R_6$ is alkyl, cycloalkyl, a phenyl group substituted with a group $R_1$, in which $R_1$ has the above-mentioned meaning, a saturated or nonsaturated heterocyclic group, or $R_5$ and $R_6$ together with the group —$NR_5$—CO— form a heterocyclic system;
- —$R_1$ and $R_2$ are alkyl, alkoxy, hydroxyl, nitro, cyano, halogen, trifluoromethyl, on the understanding that $R_1$ is the meta- and/or para-position in relation to the piperazine group;
- —m and p have the value 0–2; and
- —n is 0.

When $R_1$–$R_6$ is or comprises an alkyl group, this is preferably a straight or branched alkyl group having 1–5 carbon atoms.

As a cycloalkyl group, the groups $R_1$, $R_2$, $R_5$ and $R_6$ comprise a ring system having 3–7 ring atoms and not more than 10 carbon atoms as a whole.

When $R_1$, $R_2$, $R_4$ or $R_5$ is a hydroxyalkyl group such a group preferably comprises 1–5 carbon atoms. As a halogen atom, $R_1$, $R_2$ preferably is fluorine, chlorine or bromine.

Optionally present hydroxyl or hydroxyalkyl groups may be esterified or etherified.

Compounds which are to be preferred in particular on the basis of their properties are:
(a) 1-(benzo[b]furan-7-yl)-4-methylpiperazine;
(b) 1-[4-fluoro(benzo[b]furan-7-yl)]-4-methylpiperazine;
(c) 1-[5-fluoro(benzo[b]furan-7-yl)]-4-methylpiperazine;
(d) 1-(benzo[b]furan-7-yl)-4-(2-hydroxyethyl)piperazine;
(e) 1-(benzo[b]furan-7-yl)-4-propylpiperazine;
(f) 1-(benzo[b]furan-7-yl)-4-isopropylpiperazine;
(g) 1-[5-fluoro(benzo[b]furan-7-yl)]-4-isopropylpiperazine;
(h) 1-(benzdioxol-4-yl)-4-isopropylpiperazine;
(i) 1-(benzo[b]furan-7-yl)-4-allylpiperazine;
(j) 1-(benzo[b]furan-7-yl)-4-propargylpiperazine;
(k) 1-[4-fluoro(benzo[b]furan-7-yl)]-4-propagylpiperazine;
(l) 1-(benzdioxol-4-yl)-4-propargylpiperazine;
(m) 1-(benzo[b]furan-7-yl)-4-isobutylpiperazine;
(n) 1-(benzo[b]furan-7-yl)-4-cyclopropylmethylpiperazine;
(o) 1-(benzo[b]furan-7-yl)-4-pentylpiperazine;
(p) 1-(benzo[b]furan-7-yl)-4-[2-(2-furyl)ethyl]piperazine;
(q) 1-(benzo[b]furan-7-yl)-4-(4-chlorobenzyl)piperazine;
(r) 1-(benzo[b]furan-7-yl)-4-(2-phenylethyl)piperazine;
(s) 1-(benzo[b]furan-7-yl)-4-[2-[N-(acetyl)-N-(methyl)amino]ethyl]piperazine;
(t) 1-(benzo[b]furan-7-yl)-4-[2-[N-(pyrrolidin-2-onyl)]ethyl]piperazine;
(u) 1-(benzo[b]furan-7-yl)-4-[2-(N-succinimidyl)ethyl]piperazine;
(v) 1-(benzo[b]furan-7-yl)4-[2-[N-(oxazolidin-2-onyl)ethyl]]piperazine;
(w) 1-(benzo[b]furan-7-yl)-4-[2-[N-(4-chlorobenzoyl)-N-(methyl)amino]ethyl]piperazine;
(x) 1-(benzo[b]furan-7-yl)-4-[2-[N-(4-cyanobenzoyl)-N-(methylamino]ethyl]piperazine;
(y) 1-(benzo[b]furan-7-yl)-4-[2-[N-(4-nitrobenzoyl)-N-(methyl)amino]ethyl]piperazine;
(z) 1-(benzo[b]furan-7-yl)-4-[2-[N-(4-methoxybenzoyl)-N-(methyl)amino]ethyl]piperazine;
(aa) 1-(benzo[b]furan-7-yl)-4-[2-[N-(4-isopropylbenzoyl)-N-(methyl)amino]ethyl]piperazine;

(bb) 1-[4-fluoro(benzo[b]furan-7-yl)]-4-[2-[N-(4-isopropylbenzoyl)-N-(methyl)amino]ethyl]piperazine;
(cc) 1-(benzo[b]furan-7-yl)-4-[2-[N-(4-isopropylbenzoyl-N-(2-hydroxyethyl)amino]ethyl]piperazine;
(dd) 1-(benzo[b]furan-7-yl)-4-[2-[N-(4-isopropylbenzoyl)-N-(propyl)amino]ethyl]piperazine;
(ee) 1-(benzo[b]furan-7-yl)-4-[[N-methyl-5-(4-fluorophenyl)pyrrol-2-yl]methyl]piperazine;
(ff) 1-(benzo[b]furan-7-yl)-4-(acetylmethyl)piperazine.

Suitable acids with which the compounds according to the invention can form pharmaceutically acceptable acid addition salts are, for example, hydrochloric acid, sulphuric acid, phosphoric acid, nitric acid, and organic acids such as citric acid, fumaric acid, maleic acid, tartaric acid, acetic acid, benzoic acid, p-toluenesulphonic acid, methanesulphonic acid, naphthalenesulphonic acid and the like. Prodrugs are to be understood to be derivatives of the compounds of the formula (1) which are inactive as such, and which after administration are converted in the body into an active compound of formula (1).

When a centre of chirality is present, both the racemate and the individual enantiomers belong to the invention.

The compounds according to the invention have interesting psychotropic properties and may hence be used for the treatment of affections and diseases which are the result of disturbances in the central nervous system, for example psychoses, aggression, fear and depression.

The compounds notably have a specific antipsychotic activity which is not associated with the side effects as a result of dopaminolytic and sedative activities which generally are to be considered as undesired. Some compounds moreover have centrally mediated analgetic and/or antihypertensive properties, or have a thrombolytic effect.

The antipsychotic activity was determined in a test procedure in which the suppression of conditioned behaviour in experimental animals (rats) was measured in a manner known per se. The compounds were evaluated as active when in this test they show at least 50% suppression of the conditioned behaviour after oral administration of 50 mg per kg of body weight or less.

The dopaminolytic activity of the compounds was determined by means of behavioural or biochemical tests known per se, for example, induction of catalepsy, increase of the dopamine synthesis or conversion rate in the central nervous system, and by affinity to dopamine receptors which is determined by displacement of a radioactive labelled ligand in a tissue homogenate.

The sedative activity of the compounds was measured in a test in which their influence upon the spontaneous locomotoric activity of experimental animals is determined according to methods known per se.

It was found that the dopaminolytic and sedative side effects as a rule do not occur with dosages which are at least three times as high as those in which 50% suppression of the conditioned behaviour is found.

The quantity, frequency and way of administration may differ for each individual case, also dependent on the nature and the severity of the disturbances. In general, a dosage of 1–500 mg per day, and preferably 1–100 mg daily, may be used for humane applications in one dosage per day.

The active compounds according to the invention and their salts and prodrug forms can be processed to compositions by means of standard methods which are known per se, for example, pills, tablets, coated tablets, capsules, powders, injection liquids and the like, while using the usual auxiliary substances, for example, solid and liquid carrier materials.

The compounds and their acid addition salts, prodrugs and enantiomers can be brought into a form suitable for administration in a manner known per se.

The compounds of the formula (1) are new compounds with the exception of the compounds wherein A forms together with the two carbon atoms of the phenyl group a completely are partly unsaturated 5- or 6-membered ring which contains a nitrogen atom in the meta- or ortho-position in relation to the piperazine group as the only hetero atom, $R_1$ is halogen, nitro or lower alkoxy, $R_2$ is lower alkyl or an oxo group, n is 0, p is 0 or 1, m has the value 0–2, and B has the above mentioned meaning, which compounds are partly known from French patent specification No. 81,23744, Japanese patent specification No. 57,193459, British patent specification No. 2,086,896 and/or J. Chem. Soc., C, no. 10 (1967), pages 1003–1006.

The new compounds according to the invention can be prepared in a manner known for the synthesis of analogous compounds, for example, as described in Netherlands Patent Application No. 8005133.

The compounds can be obtained more in particular by reaction of a compound of formula 2

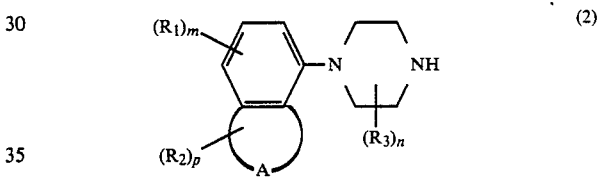

with a compound of formula L-Q, in which A, Q, $R_1$–$R_3$, m, n and p have the meanings mentioned hereinbefore, and L is a so-called leaving group, for example hydroxyl, chlorine, bromine or tosylate. This reaction may be carried out both with and without an aprotic organic solvent, optionally in the presence of an acid binder. Examples of suitable solvents are methyl ethyl ketone, tetrahydrofuran, acetonitril, dimethyl formamide, toluene and petroleum ether. As acid binders are to be considered substances can either be soluble or unsoluble in the reaction medium, for example, organic nitrogen bases, such as trialkyl amines, pyridine, urea, and inorganic bases, such as sodium or potassium carbonate or -bicarbonate. The reaction temperature usually is between room temperature and the reflux temperature of the solvent used, while the reaction duration may vary from 1 to 2 hours.

Further the compounds of the invention of the formula (1) can be obtained by reaction of a compound of the above formula (2) with a carbonyl compound of the formula B'=0 under the influence of a gentle reducing agent. In these formulae A, $R_1$–$R_3$, m, n and p have the above meaning and B'=0 results after the reaction in a group B having the above meaning. This method is suitable in particular for the preparation of compounds of formula (1) wherein Q represents a branched alkyl group or cycloalkyl group. The reaction is preferably carried out in an alcoholic solvent in the presence of a reduction agent which does not react with the carbonyl group, such as metal borohydride, preferably sodium cyanoborohydride. The reaction temperature is usually between 0° C. and reflux temperature. The reaction time varies from a few minutes to several hours.

In so far as the starting compounds of formula 2 are new, they can be obtained according to methods which are known for the synthesis of analogous compounds, for example, according to methods which are known from Netherlands Patent Applications 80.05133 and 82.01708.

The compounds of formula 1 in which A, $R_1$-$R_3$, m, n and p have the above-mentioned meanings and Q is a group of the formula D—$NR_5$—CO—$R_6$, in which D, $R_5$ and $R_6$ have the above-mentioned meanings, with the proviso that $R_5$ is not a phenyl group, are preferably prepared from the corresponding compound of formula 3,

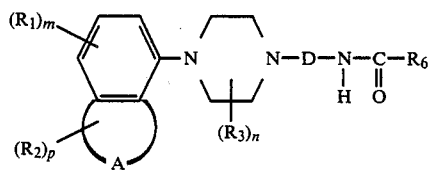

by converting this with a compound L—$R_5$, in which A, $R_1$-$R_3$, D, L, $R_5$, $R_6$, m, n and p have the abovementioned meanings. This reaction is preferably carried out in two steps. In the first step the proton of the nitrogen atom of the compound of formula 3 is removed by means of a strong organic base, for example, sodium hydride, potassium hydride or calcium hydride, or a sodium alkoxylate or potassium alkoxylate, preferably tert. butylate, in an aprotic organic solvent, for example, toluene, tetrahydrofuran, dimethylformamide or dimethylsulphoxide, at temperatures between −20° C. and the reflux temperature of the solvent. In the second step the reagent L—$R_5$ is added to the reaction mixture, the desired final product being usually obtained after a reaction time which varies from 5 minutes to a few hours.

A similar process can be used to convert compounds of the formula 3, wherein the group —NH— is replaced by a group —$CH_2$—, and the other symbols have the above mentioned meanings.

These compounds in which A, $R_1$-$R_3$, m, n and p have the above-mentioned meanings and B is a group of the formula D—$NR_5$—CO—$R_6$, in which D, $R_5$ and $R_6$ have the above-mentioned meanings, may moreover be prepared from the corresponding compounds of formula 4,

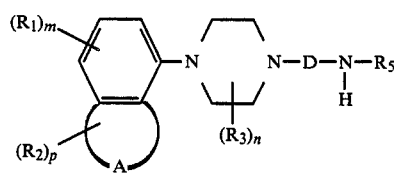

by converting them with a compound E—CO—$R_6$, in which A, $R_1$-$R_3$, D, $R_5$, $R_6$, m, n and p have the above-mentioned meanings and E is a leaving group, preferably of the type hydroxy, alkoxy, acyloxy, halogen, N-imidazolyl or N-triazolyl. This reaction is preferably carried out in an aprotic organic solvent, for example, those mentioned hereinbefore, in the presence of an acid binder, as mentioned hereinbefore, at temperatures between 0° C. and the reflux temperature of the solvent used and a reaction duration which may vary from 5 minutes to a few hours.

A further suitable method for preparing some compounds of the formula (1) is reduction of a compound of the formula 1 wherein A, Q, $R_1$-$R_3$, n, m and p have the above meanings on the understanding that Q contains a carbonyl group directly attached to the piperazine nitrogen atom. This reaction can be carried out with reducing agents such as $LiAlH_4$ or a borane-complex like $BH_3$.dimethylsulphide, in a suitable solvent, for example diethyl ether or tetrahydrofuran, at temperatures between 0° C. and the reflux temperature of the solvent used. The reaction time is usually several hours.

In so far as the starting compounds of formulae 3 and 4 are new, they can be obtained in a manner analogous to the method described hereinbefore for the preparation of compounds of formula 1, starting with a compound of formula 2.

Compounds of the formula (1) can also be obtained from precursors having formula (1) in a way known per se, for example by using hydrogenation reactions or by reactions resulting in carbon atom-hetero atom bonds in chain B via nucleophilic substitution reactions whereby the reactant containing the hetero atom functions as nucleophile.

Furthermore, some compounds of formula 1 in which at least one of the groups B, $R_1$, $R_2$, $R_4$ or $R_5$ comprises a hydroxyl function or in which B comprises an NH—$R_5$ group, can be prepared by splitting off in the last step a protective group, for example, an acetal, ketal, acyl, triphenyl methyl, trialkylsilyl, alkoxy- or trialkylsilylethyl-oxycarbonyl, by means of methods known for the purpose.

The invention will now be described in greater detail with reference to the following specific examples.

EXAMPLE I 1-benzo-[b]furan-7-yl-4[3-(4-fluorobenzoyl)propyl]piperzine HCl 7.5 Mmol (1.79 g) of 1-benzo[b]furan-7-yl-piperazine HCl, together with 9.1 mmol (1.82 g) of 1-chloro-3-(4-fluorobenzoyl)-propane, 20 mmol (2.80 g) of potassium carbonate and a catalytic quantity (approximately 100 mg) of sodium iodide as a suspension in 50 ml of methyl ethyl ketone, was heated with thorough stirring so that the solvent refluxes. After stirring for 16 hours, 9.1 mmol of 1-chloro-3-(4-fluorobenzoyl)propane and 20 mmol of potassium carbonate were added again. After stirring for another 16 hours at reflux temperature, cooling, filtering and evaporating to dryness in vacuo were carried out. The residue was chromatographed on silica gel with ethyl acetate as an eluent. After evaporating the fractions which comprised the desired product, material was obtained which was converted into the title compound via treatment with 1 equivalent of a HCl solution in ethyl acetate.

The compounds of formula 5A or 5B recorded in Table A were prepared in an analogous manner.

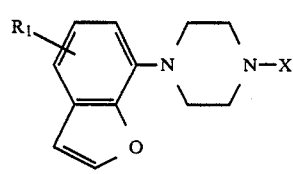

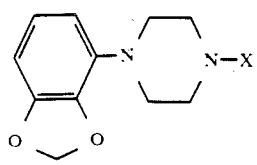

(5B)

TABLE A

| Comp. No. | Form. 5 | R₁ | X | Salt | Melt. point. (°C.) |
|---|---|---|---|---|---|
| 1 | A | H | methyl | HCl | 240–244 (decomp.) |
| 2 | B | — | methyl | HCl | 189–190 |
| 3 | A | 4-F | methyl | HCl | 161–164.5 |
| 4 | A | 5-F | methyl | HCl | 204–206.5 |
| 5 | A | H | propargyl | HCl | 204–205 |
| 6 | B | — | propargyl | HCl | 191–193 |
| 7 | A | 4-F | propargyl | HCl | 184–185.5 |
| 8 | A | H | allyl | HCl | 208–208.5 |
| 9 | A | H | n-propyl | HCl | 210–211.5 |
| 10 | A | H | 2-hydroxyethyl | HCl | 112–114 |
| 11 | A | H | 2-chloroethyl | HCl | 230–231 (decomp.) |
| 12 | A | H | acetylmethyl | HCl | 239–241 (decomp.) |
| 13 | A | H | n-pentyl | HCl | 209–210 |
| 14 | A | H | 2-ethoxyethyl | HCl | 128–132 |
| 15 | A | H | benzyl | HCl | 207.5–210 |
| 16 | B | — | benzyl | base | 60–62 |
| 17 | A | H | 4-chlorobenzyl | HCl | 232–235 (decomp.) |
| 18 | A | H | 2-phenylethyl | HCl | 242–246 |
| 19 | A | H | 2-phenyxoyethyl | HCl | 170–176 |
| 20 | A | H | —CH₂—CH₂—N(succinimido) | HCl | 155–156 |
| 21 | A | H | —CH₂—CH₂-(3-indolyl) | HCl | 233–236 |
| 22 | A | H | —CH₂—CH₂—CH₂-N(triazolinone) | 1,2 HCl | 115–122 (decomp.) |
| 23 | A | H | —CH₂-(1-methyl-5-phenylpyrrol-2-yl) | base | viscous oil |
| 24 | A | H | —CH₂-(1-methyl-5-(4-fluorophenyl)pyrrol-2-yl) | base | 118–125 |
| 25 | A | H | —CH₂-(1-methyl-5-(2,6-difluorophenyl)pyrrol-2-yl) | base | viscous oil |

TABLE A-continued

| Comp. No. | Form. 5 | R₁ | X | Salt | Melt. point. (°C.) |
|---|---|---|---|---|---|
| 26 | A | H | —CH₂—CH₂—CH₂—CH₂—N(spiro[4.5]decane-dione) | HCl | 153–160 (decomp.) |
| 27 | A | H | —CH₂—CH₂—CH(phenyl)(phenyl) | HCl | ±90 |
| 28 | A | H | —CH₂—CH₂—CH₂—CH(OH)—phenyl | HCl | 180–183 |
| 29 | A | H | —CH₂—CH₂—CH₂—C(=O)—(4-F-phenyl) | HCl | 219–220 |
| 30 | A | H | —CH₂—CH₂—N(CH₃)—CH₂—(4-Cl-phenyl) | HCl | 229–231 |
| 31 | A | H | —CH₂—CH₂—C(=O)—N(CH₃)—(4-isopropyl-phenyl) | HCl | 208–209 |
| 32 | A | H | —CH₂—CH₂—N(phenyl)—C(=O)—(4-isopropyl-phenyl) | HCl | 149–150 |

EXAMPLE II

1-Benzo[b]furan-7-yl-4-[2-[N-(4-isopropylbenzoyl)-N-(methylamino]ethyl]piperazine HCl A suspension of 75 mmol (8.55 g) of potassium hydride in mineral oil (35% KH) was washed three times with dry petroleum ether in a reaction vessel which was kept under an atmosphere of dry nitrogen. After pipetting the last quantity of petroleum ether, 70 ml of dry dimethylsuphoxide were slowly added dropwise, hydrogen gas escaping. After 15 minutes a solution of 59.2 mmol (23.2 g) of 1-benzo[b]furan-7-yl-4-[2-[N-(4-isopropylbenzoyl)amino]ethyl]piperazine in 140 ml of dry dimethylsulphoxide was rapidly added dropwise at a temperature of 20° C. A solution of 74 mmol (4.61 g) of methyl iodide in 50 ml of dry dimethylsulphoxide was added to the resulting yellow coloured solution at such a rate that the temperature of the reaction mixture remained below 30° C. After 30 minutes the reaction mixture was poured out on wateer, after which extraction with ethyl acetate was carried out. After drying these extracts over magnesium sulphate, filtration and evaporation, a cloudy oil was obtained. It was taken up in approximately 800 ml of ethyl acetate and after filtration was treated with 1 equivalent of alcoholic HCl. The title compound started to crystallize out substantially immediately. After cooling, sucking off and drying, a white powder was obtained having a melting-point of 246°–247° C. (decomposition).

The compounds of formula 6A and B recorded in Table B hereinafter were prepared in an analogous manner.

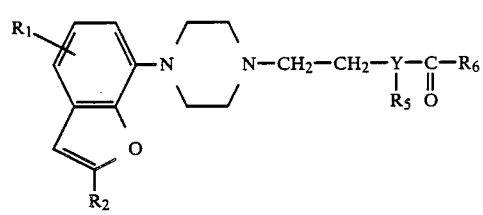

(6A)

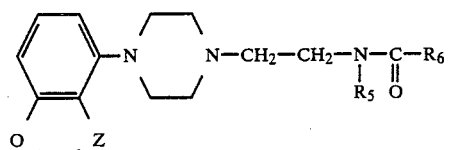

(6B)

The compounds of formula 6A listed in table C were prepared in an analogous manner:

TABLE C

| Comp. No. | Y | $R_1$ | $R_2$ | $R_5$ | $R_6$ | Salt | Melting point (°C.) |
|---|---|---|---|---|---|---|---|
| 58 | N | H | H | $CH_3$ | methyl | HCl | 192–193 |
| 59 | N | H | H | $CH_3$ | ethoxy | HCl | hygroscopic |
| 60 | N | H | H | $CH_3$ | tert.-butyl | HCl | 206–207 |
| 61 | N | H | H | $CH_3$ | 2-tetrahydrofuranyl | base | oil |
| 62 | N | H | H | $CH_3$ | 4-cyanophenyl | HCl | 230–237 |
| 63 | N | H | H | $CH_3$ | 3,4-dichlorophenyl | HCl | 228–230 |
| 64 | N | H | H | $CH_3$ | 4-bromophenyl | HCl | 127,5–128,5 |

EXAMPLE IV 1-(Benzo[b]furan-7-yl)-4-isopropylpiperazine hydrochloride 0.36 Ml of acetic acid, 0.52 g of sodium acetate and 1.0 ml of acetone were added successively to a solution of 6.28 mmol (1.50 g) of 1-(benzo[b]furan-7-yl)-piperazine hydrochloride in 20 ml of methanol at room temperature. After stirring for 30 minutes at room temperature 0.38 g of sodium cyanoborohydride were added to the reaction mixture and stirring was continued for 3 hours. After evaporation in vacuo the residue was purified by means of flash-chromatography on silica gel. The fractions containing the desired product were evaporated and the so-obtained free base was converted into the crystalline title compound by treatment with 1 equivalent of HCl in ethyl acetate.

The compounds of formulae 5A and 5B indicated in table D have been prepared in an analogous manner:

TABLE B

| Comp. No. | Form. 6 | Y | Z | $R_1$ | $R_2$ | $R_5$ | $R_6$ | Salt | Melting point (°C.) |
|---|---|---|---|---|---|---|---|---|---|
| 33 | B | — | O | — | — | $CH_3$ | 4-fluorophenyl | HCl | 190–192 |
| 34 | A | CH | — | H | H | $CH_3$ | 4-fluorophenyl | HCl | 189–190 |
| 35 | A | N | — | H | H | $CH_3$ | 4-methylsulphonylphenyl | base | visc. oil |
| 36 | A | N | — | H | H | $CH_3$ | 4-methylfenyl | HCl | 240–241 |
| 37 | A | N | — | H | H | $CH_3$ | 4-tert.butylphenyl | HCl | 240 (decomp.) |
| 38 | A | N | — | H | H | $CH_3$ | 4-ethylphenyl | HCl | 227–230 (decomp.) |
| 39 | A | N | — | H | H | $CH_3$ | phenyl | HCl | 228–230 |
| 40 | A | N | — | H | H | $CH_3$ | 4-fluorophenyl | HCl | 239–242 (decomp.) |
| 41 | A | N | — | H | H | $CH_3$ | 4-chlorophenyl | HCl | 239–240 |
| 42 | A | N | — | H | H | $CH_3$ | 4-trifluoromethylphenyl | HCl | 250 (decomp.) |
| 43 | A | N | — | H | H | $CH_3$ | 4-nitrophenyl | HCl | 226–227,5 |
| 44 | A | N | — | H | H | $CH_3$ | 4-dimethylaminophenyl | HCl | 205–211 (decomp.) |
| 45 | A | N | — | H | H | $CH_3$ | 4-methoxyphenyl | HCl | 231–233 |
| 46 | A | N | — | H | H | $CH_3$ | 3-chlorophenyl | HCl | 193–194 |
| 47 | A | N | — | H | H | $CH_3$ | 2-chlorophenyl | HCl | 214–216 |
| 48 | A | N | — | H | H | $CH_3$ | cyclohexyl | HCl | 205–206 |
| 49 | A | N | — | H | $CH_3$ | $CH_3$ | 4-chlorophenyl | HCl | 227–228 |
| 50 | A | N | — | H | $CH_3$ | $CH_3$ | 4-isopropylphenyl | HCl | 192 |
| 51 | A | N | — | 5-F | H | $CH_3$ | 4-chlorophenyl | HCl | 219–222,5 |
| 52 | A | N | — | 4-F | H | $CH_3$ | 4-isopropylphenyl | HCl | 244–249 |
| 53 | A | N | — | H | H | $C_2H_5$ | 4-isopropylphenyl | HCl | 203–204 |
| 54 | A | N | — | H | H | $C_2H_4OH$ | 4-isopropylphenyl | HCl | 137,5–138 |
| 55 | A | N | — | H | H | $n-C_3H_7$ | 4-isopropylphenyl | HCl | 174–175 |
| 56 | A | N | — | H | H | $CH_3$ | 4-isopropylphenyl | HCl | 246–247 (decomp.) |
| 57 | B | — | $CH_2$ | — | — | $CH_3$ | 4-fluorophenyl | HCl | 250–253 |

EXAMPLE III 1-(Benzo[b]furan-7-yl-4-[2-[N-(acetyl)-N-methyl-)amino]ethyl]piperazine hydrochloride 4.1 Mmol (0,62 ml) of triethylamine and 4,0 mmol (0,29 ml) of acetyl chloride were successively added to a solution of 3.7 mmol (0,96 g) of N-[2-[4-(benzo[b]furan-7-yl)-1-piperazinyl]ethyl]-N-methylamine in 50 ml of chloroform at room temperature, giving an exothermic reaction. After stirring for 15 minutes 5 ml of methanol was added and the mixture was sucked off to dryness in vacuo. The residue was treated with ether which resulted in crystallization of the obtained triethylamine hydrochloride. This was sucked off and washed with ether. The filtrate after evaporation was taken up in ethyl acetate. 1 Equivalent of hydrochloric acid was added, giving the title compound as a solid substance.

TABLE D

| Comp. No. | Form. 5 | R₁ | X | Salt | Melt. point (°C.) |
|---|---|---|---|---|---|
| 65 | B | — | isopropyl | HCl | 196–197 |
| 66 | A | 5-F | isopropyl | HCl | 188–190,5 |
| 67 | A | H | isopropyl | HCl | ±225 |
| 68 | A | H | isobutyl | HCl | 189.5–192 |
| 69 | A | H | cyclohexyl | HCl | 245–247 |

EXAMPLE V 1-(Benzo[b]furan-7-yl)-4-(cyclopropylmethyl)piperazine hydrochloride 0.28 g Of lithium aluminum hydide were added in small portions to a solution of 5.8 mmol (1.56 g) of 1-(benzo[b]furan-7-yl)-4-(cyclopropylcarbonyl)piperazine in 30 ml of dry tetrahydrofuran. The mixture was stirred until the formation of gas stopped. After adding of 5 ml of water and 50 ml of 2N sodium hydroxide the reaction mixture was extracted and the organic layers were evaporated. Chromatographic purification on silica gel resulted in 1.0 g of a viscous substance, which was converted into the title compound by treatment with 1 equivalent of HCl. in ethyl acetate.

The compounds of formula 5A mentioned in table E been prepared in similar way.

TABLE E

| Comp. No. | R₁ | X | Salt | Melt. point (°C.) |
|---|---|---|---|---|
| 70 | H | cyclopropylmethyl | HCl | 204–206 |
| 71 | H | 2-(2-furyl)ethyl | HCl | 236–241 |

EXAMPLE VI 1-(Benzo[b]furan-7-yl)-4-[2-[N-(pyrrolidin-2-onyl)]-ethyl]piperazine hydrochloride A suspension of 5 mmol (0.58 g) of potassium hydride in mineral oil (35% KH) was washed three times with dry petroleum ether in a reaction vessel which was kept under an atmosphere of nitrogen. Then 5 ml of dry dimethylsulphoxide were added dropwise giving a clear solution. 4.15 Mmol (0.315 ml) of 2-pyrrolidinon was added. After stirring for 20 minutes at room temperature 3.77 mmol (1.0 g) of 1-(benzo[b]furany-7-yl)-4-(2-chloroethyl)piperazine were added to the clear solution. After stirring for 16 hours at room temperature and 1 hour at 70° C. the mixture was poured out on a system of two phases consisting of water and ethylacetate. After extraction 1.10 g of an oil were obtained, which was purified by flash-chromatography on silica gel. The obtained substance (0.76 g) was converted with HCl in ethanol. The title compound was obtained after crystallization from a mixture of ethanol and ethyl acetate.

The compounds of the formula 5A mentioned in table F were prepared in a similar way:

TABLE F

| Comp. No. | R₁ | X | Salt | Melt. point (°C.) |
|---|---|---|---|---|
| 72 | H | —CH₂—CH₂—N(pyrrolidin-2-onyl) | 1.5HCl | 223–224 |
| 73 | H | —CH₂—CH₂—N(oxazolidin-2-onyl) | HCl | 138 (decomp.) |
| 74 | H | —CH₂—CH₂—N(7-chloro-isoquinolin-1(2H)-onyl) | base | 152–153 |

What is claimed is:

1. A method of treating affections and diseases which are the result of disturbances in the central nervous system, characterized in that it comprises as active substance, a compound of the formula (1) is used;

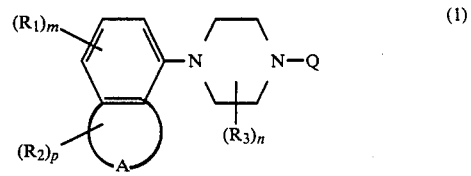

wherein:

A together with the two carbon atoms of the phenyl group forms a 5-membered unsaturated ring having one or two hetero atoms of the group O, N and S;

Q is a straight, branched or cyclic, saturated or unsaturated chain of 1–10 carbon atoms and 0–3 N and/or O atoms, which chain may be substituted with a keto group, 1–6 halogen atoms, 1–3 phenyl groups which may be substituted with 1–2 substituents selected from alkyl with 1–5 carbon atoms, halogen, trifluoromethyl, nitro, cyano, dimethylamino and methylsulfonyl, or the chain may be substituted with one mono- or bicyclic heterocyclic group with 5–10 ring atoms of which 1–4 are hetero atoms of the group N, O or S, which heterocyclic group may be substituted with 1–3 alkyl or alkoxy groups with 1–5 carbon atoms, keto groups, or with a phenyl group which may be substituted with 1–3 halogen atoms, with the proviso that chain nitrogen atoms are substituted with 1 or 2 alkyl or hydroxyalkyl groups with 3-7 carbon atoms, or with a phenyl group;

$R_1$ and $R_2$ may be alkyl or alkoxy with 1-5 carbon atoms, hydroxyl, nitro, cyano, halogen, trifluoromethyl;

m has the value 0-1;

p has the value 0-1;

$R_3$ is an alkyl group having 1-5 carbon atoms; and n has the value 0-2, or a pharmaceutically acceptable acid addition salt thereof.

2. The method according to claim 1, characterized in that it contains:

(a) 1-(benzo[b]furan-7-yl)-4-methylpiperazine;
(b) 1-[4-fluoro(benzo[b]furan-7-yl)]-4-methylpiperazine;
(c) 1-[5-fluoro(benzo[b]furan-7-yl)]-4-methylpiperazine;
(d) 1-(benzo[b]furan-7-yl)-4-(2-hydroxyethyl)piperazine;
(e) 1-(benzo[b]furan-7-yl)-4-propylpiperazine;
(f) 1-(benzo[b]furan-7-yl)-4-isopropylpiperazine;
(g) 1-[5-fluoro(benzo[b]furan-7-yl)]-4-isopropylpiperazine;
(h) 1-(benzdioxol-4-yl)-4-isopropylpiperazine;
(i) 1-(benzo[b]furan-7-yl)-4-allylpiperazine;
(j) 1-(benzo[b]furan-7-yl)-4-propargylpiperazine;
(k) 1-[4-fluoro(benzo[b]furan-7-yl)]-4-propagylpiperazine;
(l) 1-(benzdioxol-4-yl)-4-propargylpiperazine;
(m) 1-(benzo[b]furan-7-yl)-4-isobutylpiperazine;
(n) 1-(benzo[b]furan-7-yl)-4-cyclopropylmethylpiperazine;
(o) 1-(benzo[b]furan-7-yl)-4-pentylpiperazine;
(p) 1-(benzo[b]furan-7-yl)-4-[2-(2-furyl)ethyl]piperazine;
(q) 1-(benzo[b]furan-7-yl)-4-(4-chlorobenzyl)piperazine;
(r) 1-(benzo[b]furan-7-yl)-4-(2-phenylethyl)piperazine;
(s) 1-(benzo[b]furan-7-yl)-4-[2-[N-(acetyl)-N-(methyl)amino]ethyl]piperazine;
(t) 1-(benzo[b]furan-7-yl)-4-[2-[N-(pyrrolidin-2-onyl)]ethyl]piperazine;
(u) 1-(benzo[b]furan-7-yl)-4-[2-(N-succinimidyl)ethyl]piperazine;
(v) 1-(benzo[b]furan-7-yl)4-[2-[N-(oxazolidin-2onyl)ethyl]]piperazine;
(w) 1-(benzo[b]furan-7-yl)-4-[2-[N-(4-chlorobenzoyl)-N-(methyl)amino]ethyl]piperazine;
(x) 1-benzo[b]furan-7-yl)-4-[2-[N-(4-cyanobenzoyl)-N-(methylamino]ethyl]piperazine;
(y) 1-(benzo[b]furan-7-yl)-4-[2-[N-(4-nitrobenzoyl)-N-(methyl)amino]ethyl]piperazine;
(z) 1-(benzo[b]furan-7-yl)-4-[2-[N-(4-methoxybenzoyl)-N-(methyl)amino]ethyl]piperazine;
(aa) 1-(benzo[b]furan-7-yl)-4-[2-[N-(4-isopropylbenzoyl)-N-(methyl)amino]ethyl]piperazine;
(bb) 1-[4-fluoro(benzo[b]furan-7-yl)]-4-[2-[N-(4-isopropylbenzoyl)-N-(methyl)amino]ethyl]piperazine;
(cc) 1-(benzo[b]furan-7-yl)-4-[2-[N-(4-isopropylbenzoyl-N-(2-hydroxyethyl)amino]ethyl]piperazine;
(dd) 1-(benzo[b]furan-7-yl)-4-[2-[N-(4-isopropylbenzoyl)-N-(propyl)amino]ethyl]piperazine;
(ee) 1-(benzo[b]furan-7-yl)-4-[[N-methyl-5-(4-fluorophenyl)pyrrol-2-yl]methyl]piperazine or;
(ff) 1-(benzo[b]furan-7-yl)-4-(acetylmethyl)piperazine and pharmaceutically acceptable acid addition salts thereof.

* * * * *

UNITED STATES PATENT AND TRADEMARK OFFICE
CERTIFICATE OF CORRECTION

PATENT NO. : 4,782,061
DATED : November 1, 1988
INVENTOR(S) : Cornelis G. KRUSE, et al It is certified that error appears in the above-identified patent and that said Letters Patent is hereby corrected as shown below:

In Claim 1 of the patent, first line of column 15, between "with" and "3-7" insert -- 1-5 carbon atoms, or cycloalkyl groups with --.

Signed and Sealed this

Nineteenth Day of October, 1993

Attest:

BRUCE LEHMAN

Attesting Officer

Commissioner of Patents and Trademarks